United States Patent
Alshatwi et al.

(10) Patent No.: US 9,193,949 B1
(45) Date of Patent: Nov. 24, 2015

(54) METHOD OF MAKING A THREE-DIMENSIONAL SCAFFOLD FOR THREE-DIMENSIONAL CELL CULTURE

(71) Applicant: KING SAUD UNIVERSITY, Riyadh (SA)

(72) Inventors: Ali A. Alshatwi, Riyadh (SA); Vaiyapuri Subbarayan Periasamy, Riyadh (SA); Jegan Athinarayanan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/618,988

(22) Filed: Feb. 10, 2015

(51) Int. Cl.
*B01J 20/00* (2006.01)
*C01B 15/14* (2006.01)
*C01B 33/20* (2006.01)
*C12N 5/00* (2006.01)
*C01B 33/12* (2006.01)

(52) U.S. Cl.
CPC ............ *C12N 5/0075* (2013.01); *C01B 33/126* (2013.01); *C12N 2513/00* (2013.01); *C12N 2533/90* (2013.01)

(58) Field of Classification Search
CPC .............................. C01B 33/113; C01B 33/18
See application file for complete search history.

(56) References Cited

U.S. PATENT DOCUMENTS

| | | | |
|---|---|---|---|
| 5,656,568 A * | 8/1997 | Shiuh et al. | 502/412 |
| 8,492,444 B2 | 7/2013 | Hammond et al. | |
| 2012/0041081 A1 * | 2/2012 | Hammond et al. | 514/783 |

OTHER PUBLICATIONS

Saravanan et al (Producing nanosilica from Sorghum vulgare seed heads, Powder Technology 224 (2012) 345-350.*
Parry et al., "The Distribution of Silicon Deposits in the Roots of Molinia caerulea (L.) Moench. and Sorghum bicolor (L.) Moench.", Ann. Bot., 39(5), 995-1001, 1975.
Lux et al., "Silicification in sorghum (Sorghum bicolor) Cultivars with Different Drought Tolerance", Physiologia Plantarum, 115(1), 87-92, 2002.

* cited by examiner

*Primary Examiner* — Melvin C Mayes
*Assistant Examiner* — Michael Forrest
(74) *Attorney, Agent, or Firm* — Ricard C. Litman

(57) ABSTRACT

The method of making a three-dimensional scaffold for three-dimensional cell culture includes obtaining amorphous silica from *sorghum* husks, producing biogenic silica microbodies from the amorphous silica, and clustering the biogenic silica microbodies to form the three-dimensional scaffold. The three-dimensional scaffold can be used for growing three-dimensional cell cultures, such as human mesenchymal stem cell cultures.

10 Claims, 11 Drawing Sheets

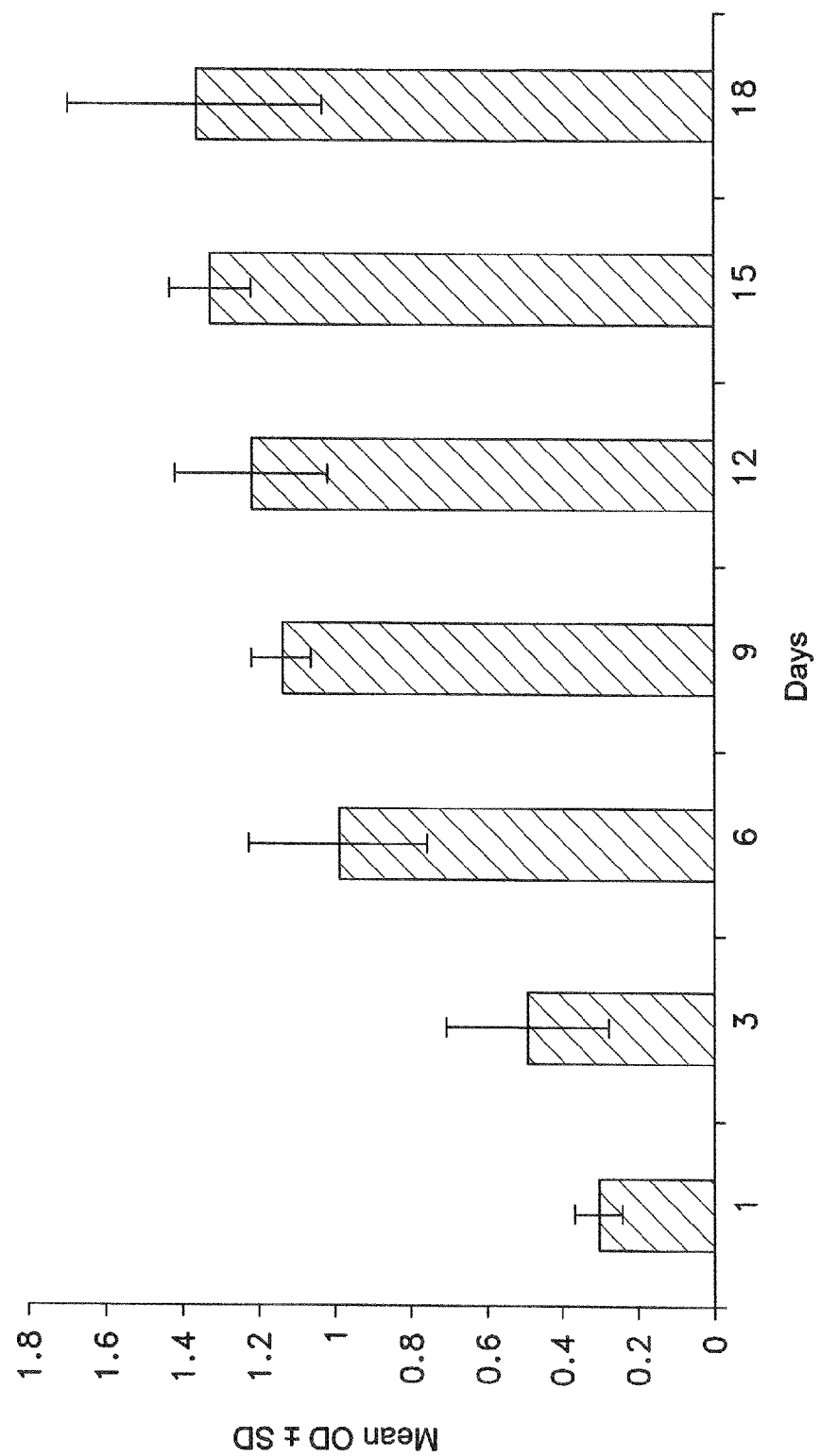

METHOD OF MAKING A THREE-DIMENSIONAL SCAFFOLD FOR THREE-DIMENSIONAL CELL CULTURE

BACKGROUND OF THE INVENTION

1. Field of the Invention

The present invention relates to the formation of a three-dimensional, biocompatible scaffold, and particularly to a method of making a three-dimensional scaffold from biogenic silica derived from *sorghum* husks.

2. Description of the Related Art

Bio-silicification and bio-mineralization are inorganic polymerization processes occurring in multicellular organisms, such as plants, animals, diatoms and sponges. These processes occur at normal physiological conditions and result in a wide range of natural composites and morphological frameworks. Such "silica super-structures" are typically not reproducible by artificial methods. Until recently, the relatively large quantities of biogenic silica ($BSiO_2$) present in agricultural biomass or byproducts generated from the waste of agricultural crops was seen as nothing more than a pollution problem. However, such biomass resulting from the processing of sugarcane waste, rice husks, millet waste, *sorghum* husks, etc. are, in fact, a rich source of amorphous silica. The silica produced in this manner may be extracted in a more economically efficient manner than typical geological silica sources.

In general, biogenic amorphous silica bodies are more useful than crystalline silica structures because the amorphous silica has a relatively high surface area and is highly reactive due to nano-scale interactions. Biogenic silica bodies are mostly found in amorphous, fibrous, porous and hydrated forms [$BSiO_2.nH_2O$] and are typically in the form of polymerized materials (on the order of 10-1000 μm) produced by natural-silicification processes. Agricultural crops, such as millet, sugarcane, *sorghum*, etc., have high concentrations of non-toxic and biocompatible silica, typically found at about 5 to 75% of the total mineral content.

Common materials used for three-dimensional culture models are typically derived from various natural or synthetic sources, such as polymers, polyethylene glycol, inorganic composites, chitosan, collagen, alginate, organic hydrogels and nanofibers. However, the lack of multiple-functionalization, limited surface modification, poor mechanical strength, chemical hydrolysis, lack of biocompatibility, insensitivity to enzymatic processes, lack of cell specificity, biodegradability, and limited processability make these materials inefficient and often ineffective for their intended purpose.

Thus, a method of making three-dimensional scaffold for three-dimensional cell culture solving the aforementioned problems is desired.

SUMMARY OF THE INVENTION

The method of making a three-dimensional scaffold for three-dimensional cell culture includes obtaining amorphous silica from *sorghum* husks, producing biogenic silica microbodies from the amorphous silica, and clustering the biogenic silica microbodies to form the three-dimensional scaffold. The three-dimensional scaffold can be used for growing three-dimensional cell cultures, such as human mesenchymal stem cell cultures.

These and other features of the present invention will become readily apparent upon further review of the following specification.

BRIEF DESCRIPTION OF THE DRAWINGS

FIG. 5 is a graph illustrating cell growth and viability, represented by mean optical density via MTT assay, for human mesenchymal stem cells (hMSCs) cultured and grown on the three-dimensional scaffold produced in accordance with the present teachings.

Unless otherwise indicated, similar reference characters denote corresponding features consistently throughout the attached drawings.

DETAILED DESCRIPTION OF THE PREFERRED EMBODIMENTS

Figure 1A:
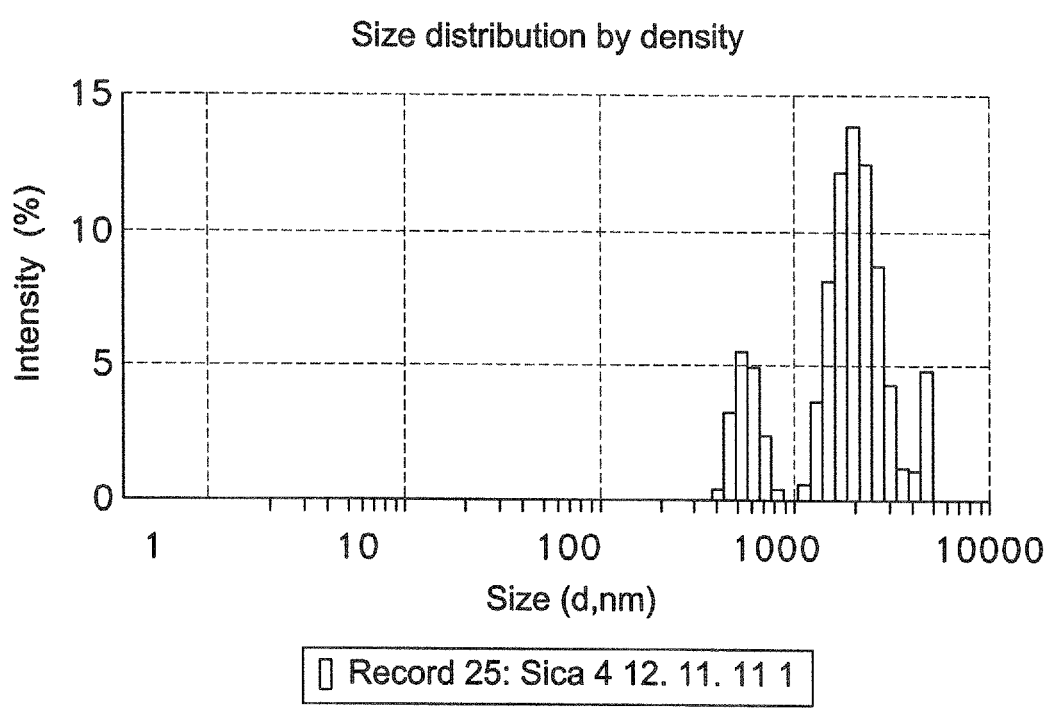
FIG. 1A is a graph of size distribution of biogenic silica microbodies obtained in accordance with the present teachings.

A method of making a three-dimensional scaffold for three-dimensional cell culture includes obtaining amorphous silica from *sorghum* husks, producing biogenic silica microbodies from the amorphous silica, and clustering the biogenic silica microbodies to form the three-dimensional scaffold. The three-dimensional scaffold can be used for growing three-dimensional cell cultures, such as human mesenchymal stem cell cultures.

The *sorghum* husks can be husks of *Sorghum bicolor*. As described in further detail below, biogenic silica bodies can be extracted from the *sorghum* husks by first washing and then drying the *sorghum* husks. The washed and dried *sorghum* husks can then mixed with hydrochloric acid and heated under pressurized conditions to produce acid-digested *sorghum* husks. The acid-digested *sorghum* husks can be washed to remove residual hydrochloric acid, and then dried and calcined to produce amorphous silica residue. Flux-calcination and, optionally, gradient centrifugation methods can be performed on the amorphous silica residue to produce biogenic silica microbodies, which are then clustered to form the three-dimensional scaffold.

The biogenic silica bodies have an amorphous nature, large specific surface area, hydrophilicity, flexible silanization chemistries, low auto-fluorescence and improved binding kinetics over planar surfaces for cell-adhesion, low nonspecific binding with biological molecules, and relatively easy manipulation for conjugation with chemicals. The surfaces and pores of the silica bodies can provide three-dimensional scaffold structures, which can facilitate specific cell attachment, proliferation, migration, and three-dimensional growth of cells. Three-dimensional scaffolds constructed from biogenic silica bodies, as described herein, can be biocompatible, immunologically inert, and provide supportive cell outgrowth.

The three-dimensional scaffold for three-dimensional cell culture was prepared by the present inventors as follows. After collecting the *sorghum* husks, the *sorghum* husks were washed to remove unwanted fine sands and dust materials, using tap water. The *sorghum* husks were then dried in a hot air oven at temperatures between approximately 90° C. and approximately 120° C. for approximately 8 to 12 hours. Approximately 200 grams (per batch) of *sorghum* husks were mixed with 1000 mL of 1 N hydrochloric acid (HCl) under magnetic stirring. These mixtures were transferred to a pressure cooker (autoclave) and maintained at a temperature of approximately 120° C. for approximately 30 minutes under pressure (15 lbs).

After the reaction was complete, the acid-digested *sorghum* husks were washed with ultrapure water until complete removal of the HCl was achieved. The resultant samples were dried in a hot air oven at a temperature between approximately 90° C. and approximately 100° C. for a period of 3 to 4 hours. Subsequently, the dried samples were incinerated in a calcination process at different temperatures, ranging between approximately 400° C. and 700° C. for differing time periods, ranging between 15 minutes and 3 hours in a muffle furnace, after which brown to white color amorphous silica residues were obtained. Further, a flux-calcination process was also used for preparing pure $BSiO_2$ microbodies (10 μm to 1 mm in diameter), and these were subjected to fractionation and characterization with different spectroscopic techniques.

For isolation and purification of the pure bodies, glycerol density gradient and layering were prepared from different percentages of glycerol solution in 14 mL polycarbonate tubes, from the bottom upwards, in a centrifuge. These were allowed to stand for between 30 minutes and an hour at room temperature. Suspensions of the samples were layered on the surfaces of each of the gradients and gently stirred at the sample/gradient junction to reduce discontinuity in density. Layered samples were centrifuged at between 100 rpm and 700 rpm for 5 to 10 minutes at a temperature of 25° C. in a swing-out rotor. 0.5 mL fractions were collected for each sample. Consistency of each layer was cross checked for the specific silica microbodies with material microscopy, and further subjected to fractionation and characterization with different spectroscopic techniques. Fractions of interest were successively pooled during the entire process and subjected to further characterization procedures, such as Fourier transform infrared spectroscopy (FT-IR) and X-ray diffraction (XRD) for physical-chemical properties, and bright field microscopy for morphological analysis.

Specifically, for the physical-chemical characterization of the purified $BSiO_2$ bodies, the chemical composition, phase and different chemical impurities associated with the $BSiO_2$ microstructures were characterized by using energy dispersive X-ray analysis (EDX), X-ray diffraction (XRD) and Fourier transform infrared spectroscopy (FT-IR) techniques. The surface morphology, particle size and diameter of the different $BSiO_2$ microbodies were characterized by using light microscopy, scanning electron microscopy (SEM) and transmission electron microscopy (TEM). Dynamic light scattering technology was used to determine the particle size distribution and zeta potential. A well-dispersed and agglomerate-free suspension of the $BSiO_2$ microbodies were obtained using ultrasonication and the particle size distribution, surface charge, hydrophilic characteristic and zeta potential were analyzed using a Zetasizer® Nano ZS90, manufactured by Malvern Instruments® Ltd. of the United Kingdom. Further, pooled sinuous-containing samples were washed three times using ultrasonication under phosphate-buffered saline (PBS) and cell culture media in order to remove impurities.

Figure 1B:
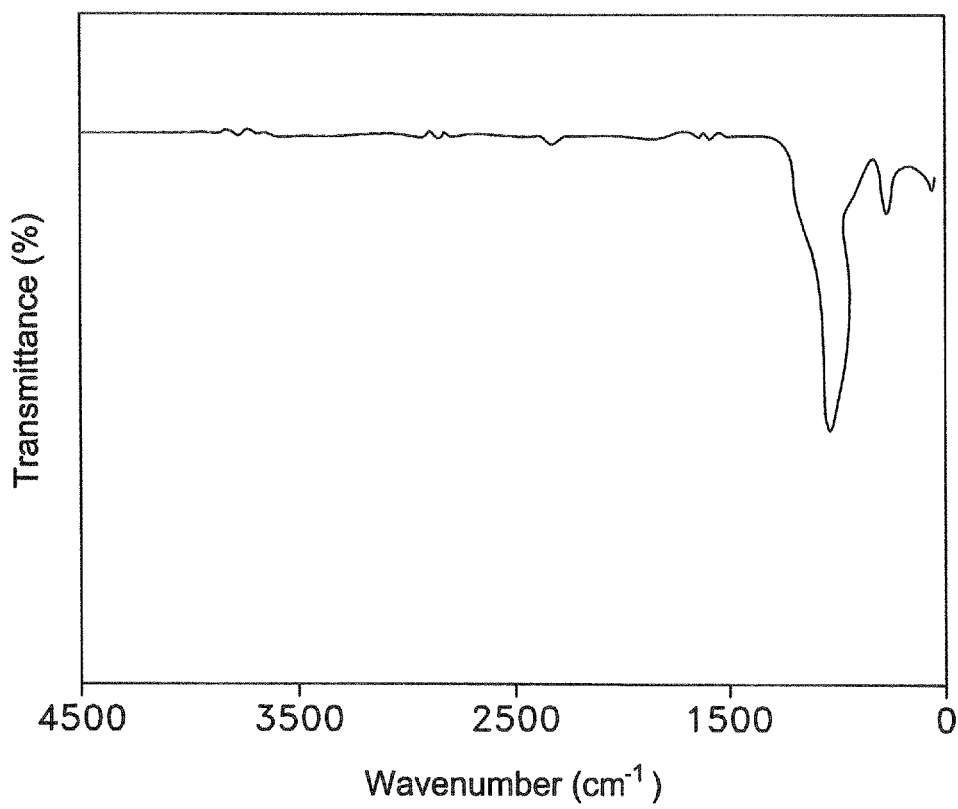
FIG. 1B is a graph showing Fourier transform infrared spectroscopy (FT-IR) of the biogenic silica microbodies obtained in accordance with the present teachings.

As noted above, both light microscopy and the Zetasizer® Nano ZS90 were used for analysis of shape, size and surface morphology of the silica bodies produced from the *sorghum* husks. 100-1000 μm microstructures were found, having various sizes and shapes, including sinuous shapes. The size distribution is shown in FIG. 1A. Predominantly, after the gradient centrifugation process, sinuous-shaped microstructures were obtained from the successfully calcined samples. The FT-IR spectra, shown in FIG. 1B, of the husks and the acid-digested *sorghum* husks show the presence of organic matter and silica. Furthermore, the prepared silica showed a peak in between 1056-1078 $cm^{-1}$ and 790-800 $cm^{-1}$, corresponding to O—Si—O stretching and Si—O bending vibration modes, respectively. No organic compounds were detected and the IR spectra of the prepared samples were almost identical. As shown in Table 1 below, 95.65% of the total content observed in the calcinated samples was silica.

TABLE 1

Total Silica Content Analysis

| Ref No | Plant Materials | Silica % | Method Ref. |
| --- | --- | --- | --- |
| ALI-003-RSW | Sorghum Red (Raw) | 4.57 | AOAC-955-03 |
| ALI-003-C | Sorghum Red (Purified) | 95.65 | AOAC-955-03 |

Figure 2A:
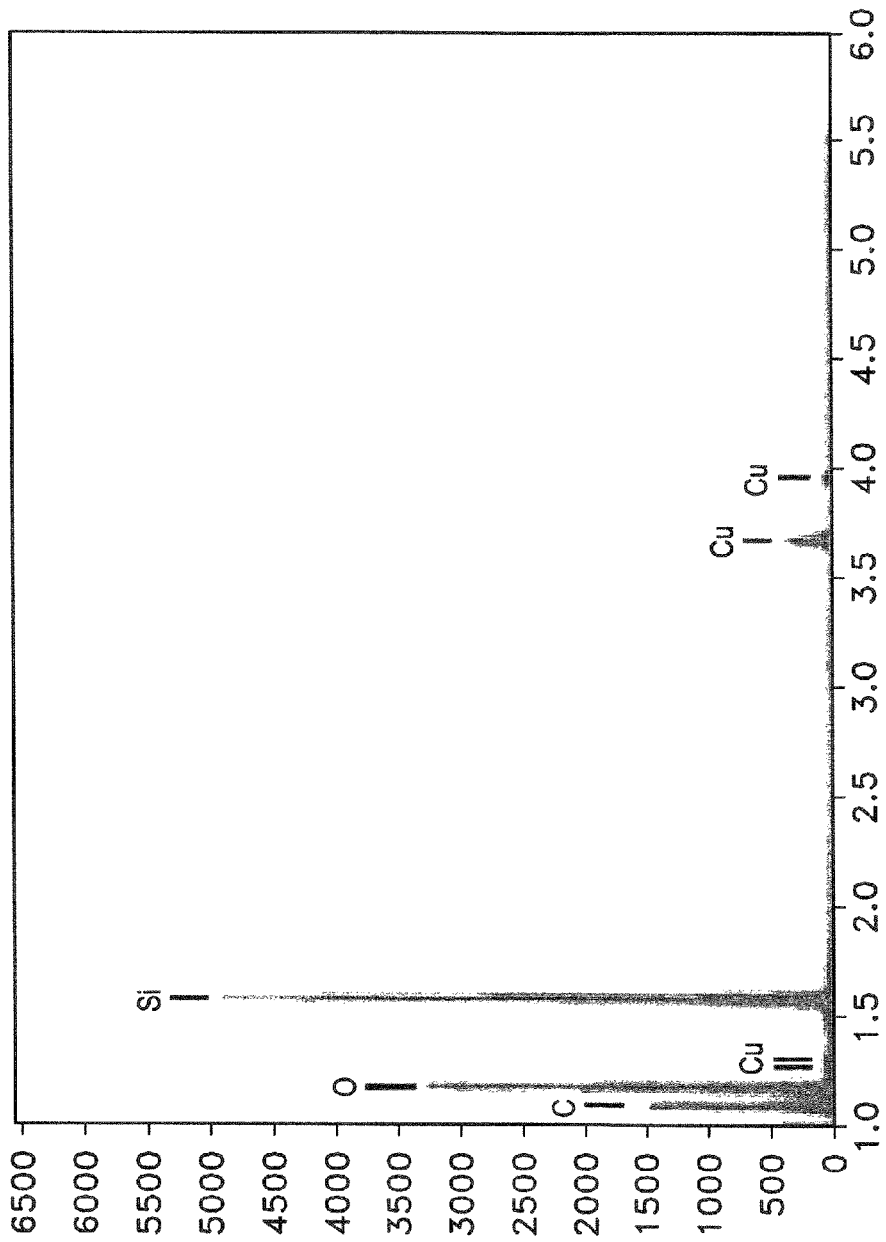
FIG. 2A is a graph showing elemental profiles generated by energy dispersive X-ray (EDX) analysis of the biogenic silica microbodies obtained in accordance with the present teachings.
Figure 2B:
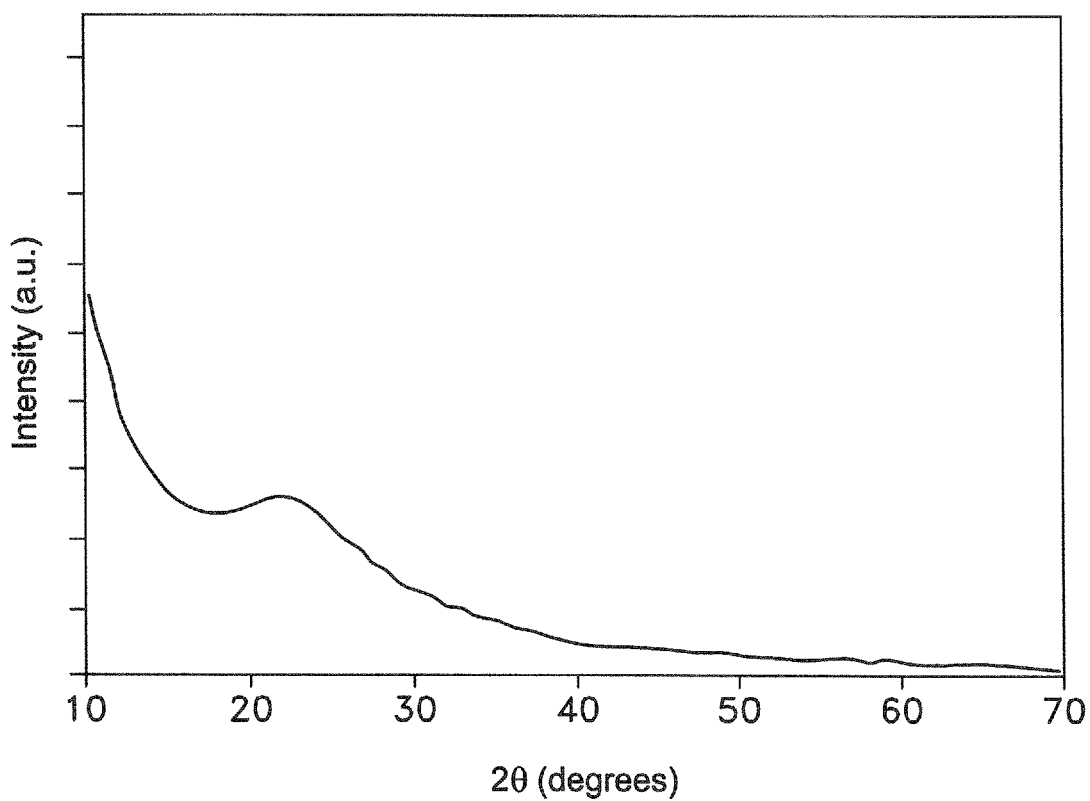
FIG. 2B is a graph showing X-ray diffraction (XRD) analysis of the biogenic silica microbodies obtained in accordance with the present teachings.
Figure 3:
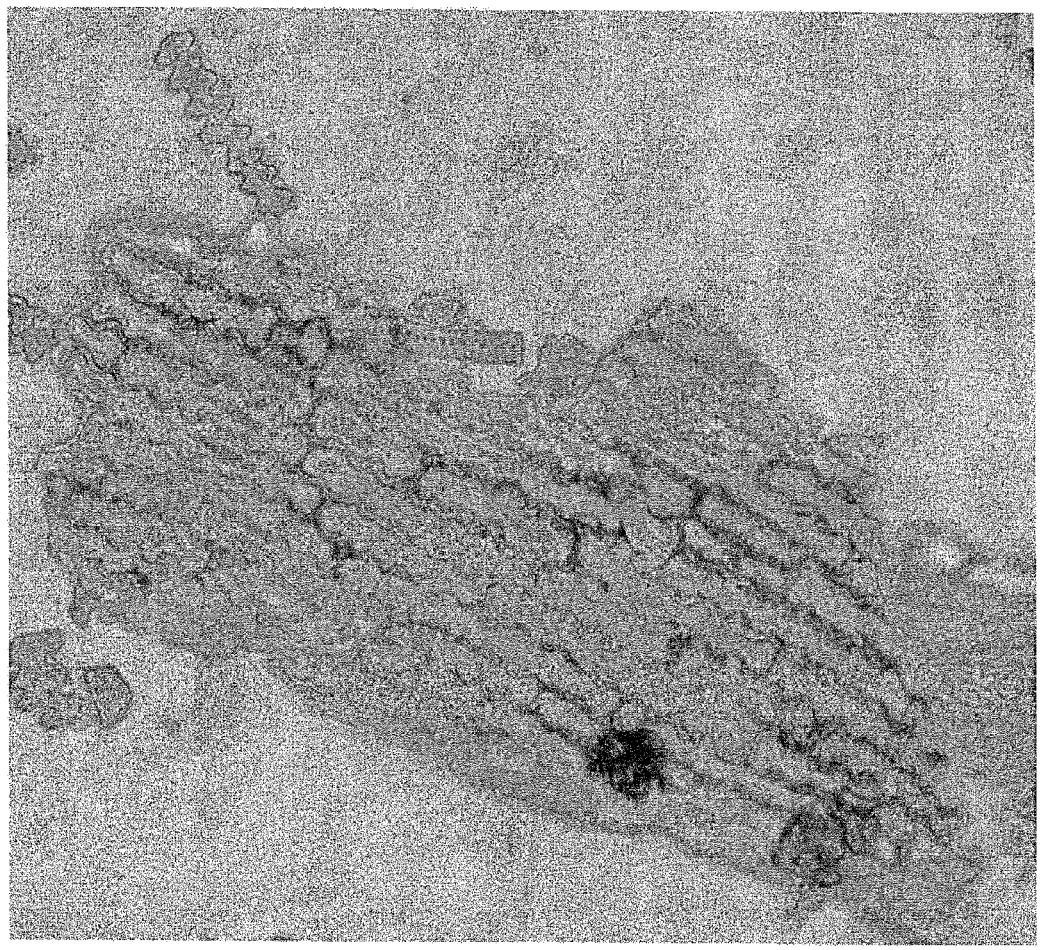
FIG. 3 is a bright field microscope image of the biogenic silica microbodies obtained in accordance with the present teachings.
Figure 4:
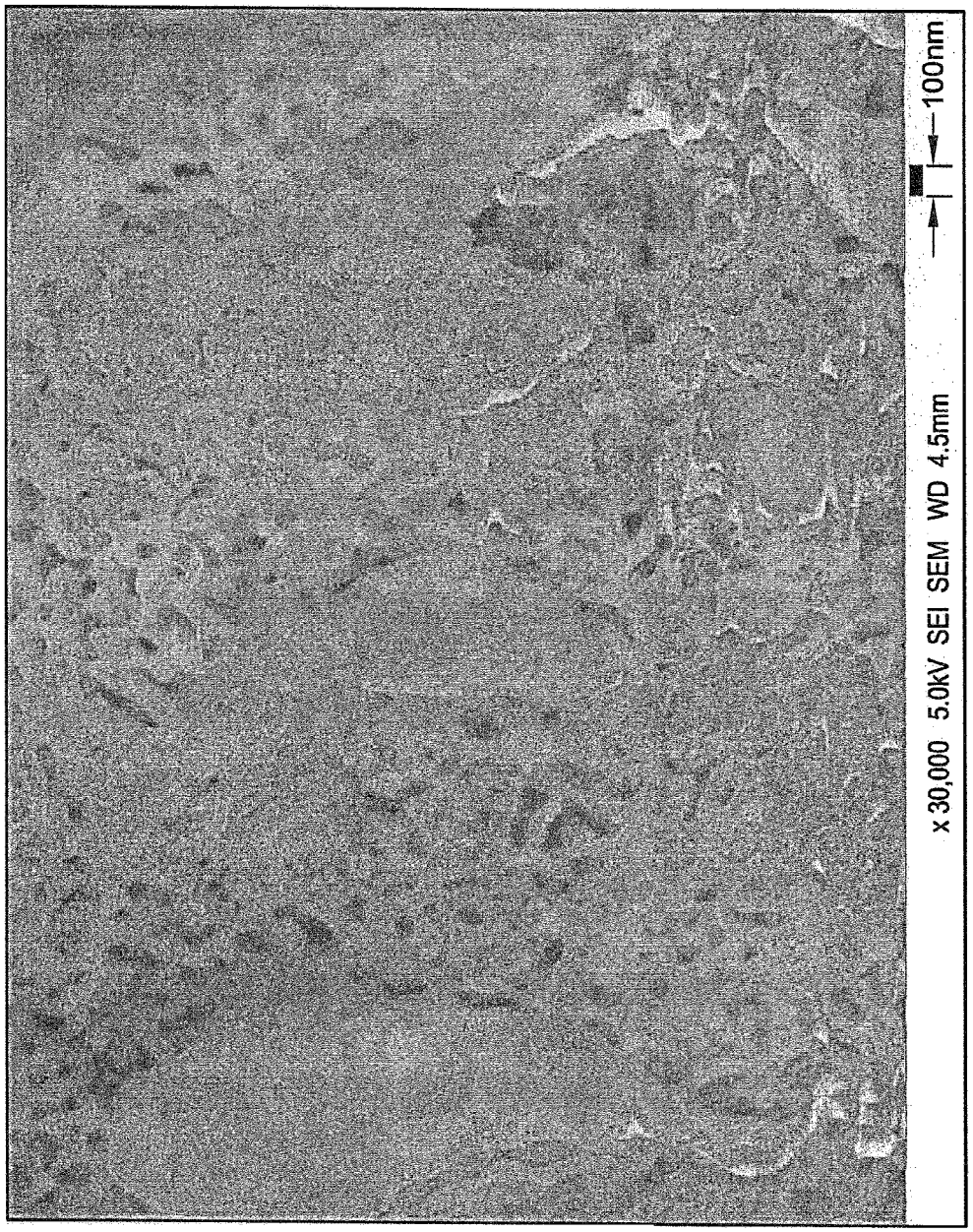
FIG. 4 is a scanning electron microscope (SEM) image of the biogenic silica microbodies obtained in accordance with the present teachings.

The elemental profiles of the prepared $BSiO_2$ microbodies were analyzed using EDX. As shown in FIG. 2A, the observed peaks indicate the presence of carbon, copper and silica elements. According to EDX analysis, the copper and carbon elements correspond to carbon-coated copper grids. The XRD pattern of the prepared biogenic silica microbodies are shown in FIG. 2B. The prepared samples show a peak with a 2θ value of 22°, corresponding to silica micro-particles. No other impurities were detected. The results revealed an amorphous nature. Broad XRD peaks of $BSiO_2$ confirmed that the prepared biogenic silica was in micro-scale. SEM confirmed a surface with a nano-scaled pattern. FIG. 3 is a bright field microscope image showing the clumped, sinuous structure. FIG. 4 is the SEM image showing the sinuous-structured surface. Thus, the experimental results confirmed that the prepared samples were amorphous and micro-structured silica particles.

In order to prepare a three-dimensional spheroid culture, human mesenchymal stem cells (hMSCs) were cultured in Eagle's minimum essential medium (EMEM) with 10% fetal bovine serum (FBS), 100 U/mL penicillin and 100 g/mL streptomycin in non-adherent cell culture dishes (both 30 mm and 60 mm well culture plates) at 37° C. in a humidified atmosphere containing 5% $CO_2$. Sinuous-shaped microparticles were clumped in the culture plates, with the individual particles being close enough to one another to form spherically-shaped porous microstructures for use as scaffold.

hMSC cells were seeded with a density range of between $25\times10^4$ and $4\times10^6$ and were cultured in order to obtain three-dimensional spheroid shapes ($BSiO_2$) in 5 mL and 10 mL of the culture media, respectively.

Three-dimensional cultures were developed in an incubator at 37° C. with 5% $CO_2$ for eighteen days, and fresh media was replenished every three days without disturbing the colonies. The growth of the three-dimensional culture on the surface of the silica microbodies was assessed by observing formation in three-dimensional [$BSiO_2$] body containing wells. Every alternate day, the morphology, size and number of the three-dimensional constructs were analyzed using an inverted microscope with an apoptome three-dimensional image analyzer. At the end of the harvesting, the three-dimensional culture was trypsinized and average cell concentrations/spheroids were determined using a microplate reader. Light microscopy and SEM images confirmed that the silica bodies had high surface areas and were highly reactive due to their nanoscale interactions with the hMSC cells.

In order to assay the cell viability, the hMSC cells were cultured on the surface of the $BSiO_2$ microbodies for 18 days. Every two days, three-dimensional cultured constructs were harvested using trypsin and transferred to 96 well plates. Then, 20 μL of 3-(4,5-dimethylthiazol-2-yl)-2,5-diphenyltetrazolium bromide (MTT) solution (5 mg/mL) in phosphate-buffered saline (PBS) was added to each well. The plates were wrapped with aluminum foil and incubated overnight at 37° C. After incubation, the plates were centrifuged and supernatants were carefully removed. Purple color formazan crystals were dissolved by the addition of 100 μL of dimethyl sulfoxide (DMSO) to each well. The absorbance was monitored at 570 nm (measurement) and 630 nm (reference) using a multiwall plate reader. Data was collected for three replicates each and used to calculate the mean standard deviation (±SD).

The spheroid culture morphologies were observed using bright field, phase contrast and fluorescent microscopy. The hMSC cells were seeded in 33 mm non-adherent plates for culturing on the surface of $BSiO_2$ microbodies for 18 days. Every two days, the three-dimensional cultured constructs were stained with acridine orange/ethidium bromide (AO/EB) at 37° C. for 5 to 10 minutes. These stained three-dimensional cultures were examined in an inverted fluorescence microscope. The size, shape and cell numbers of hMSCs were compared with each three-dimensional shaped cultured construct for 18 days. The results are presented as a representation from a series of three separate experiments. For three-dimensional culture analysis, the three-dimensional cultured constructs were harvested every two days. The data presented is representative of those obtained in at least three independent experiments conducted in triplicate.

In order to show the biocompatibility of the $BSiO_2$ microbodies, a colorimetric-based MTT assay was used. The results are illustrated in FIG. 5. For cell viability assessment, hMSC cells were cultured on the three-dimensional shaped silica surface for 18 days, and there was significant increase in the optical density (OD) value from day one to day eighteen. The growth and cell number results indicated that the $BSiO_2$ microbodies have a high biocompatibility with hMSCs.

Figure 6A:
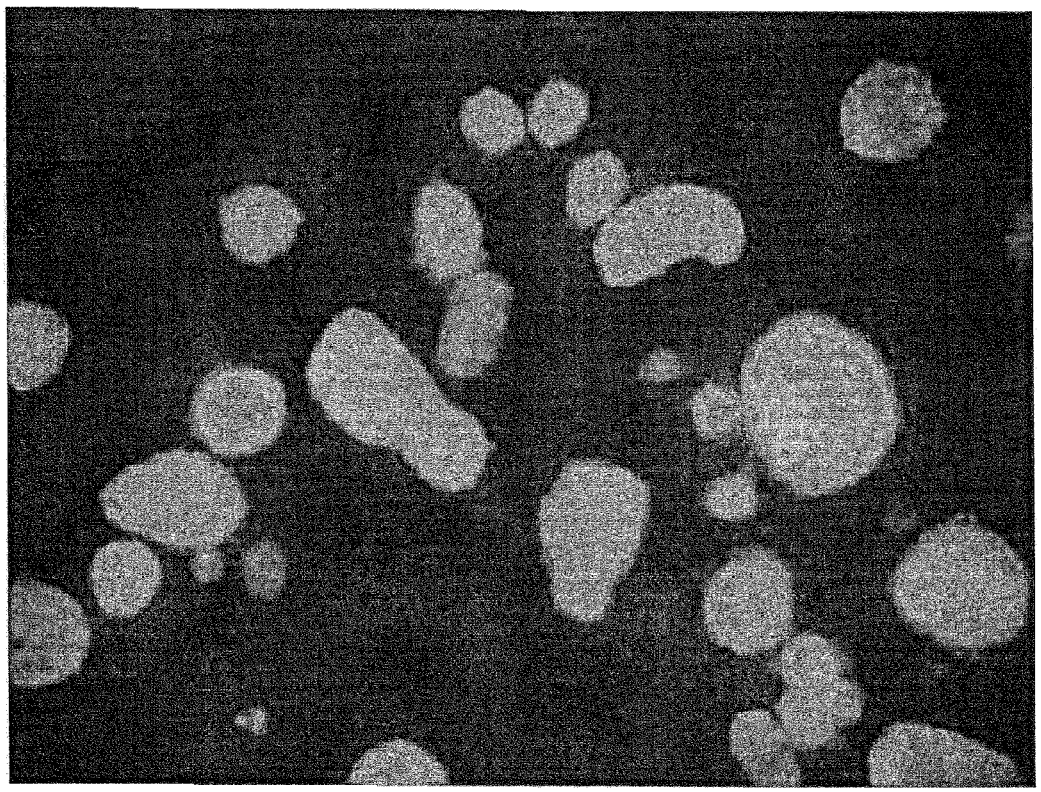
FIG. 6A is a fluorescent microscope image of the human mesenchymal stem cells (hMSCs) cultured and grown on the three-dimensional scaffold after five days.
Figure 6B:
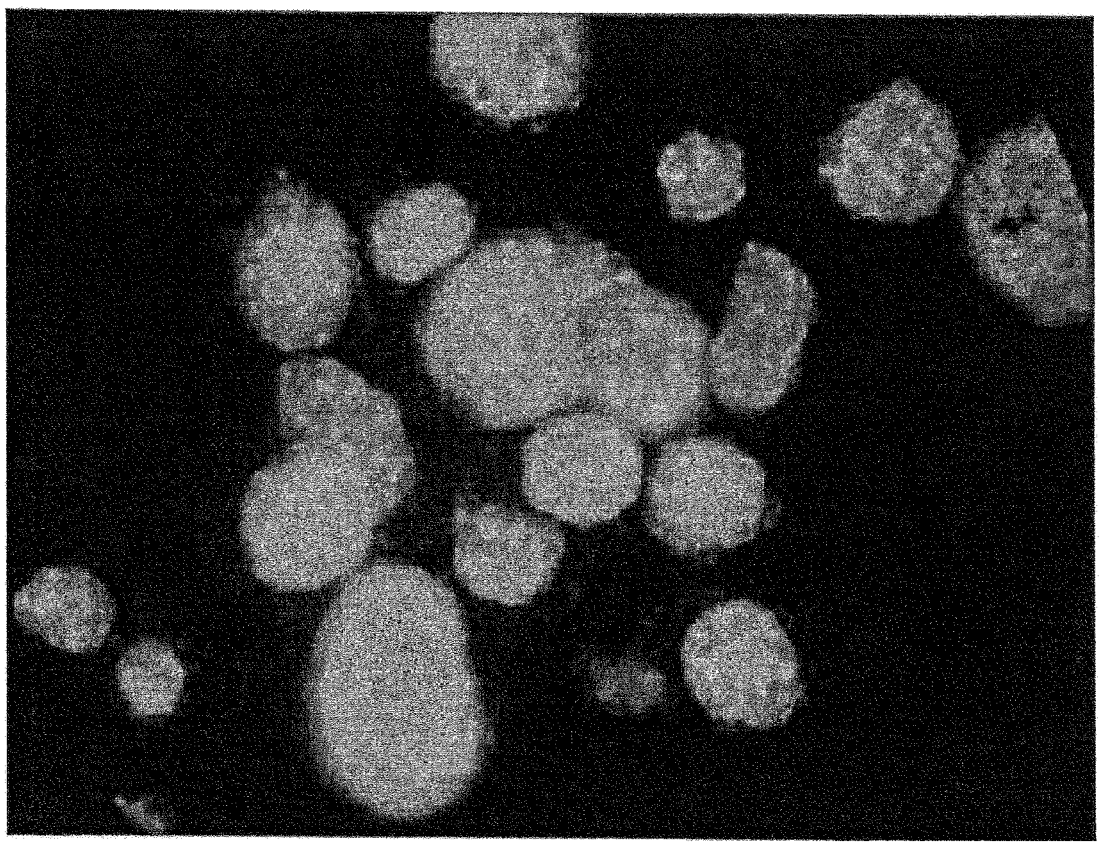
FIG. 6B is a fluorescent microscope image of the human mesenchymal stem cells (hMSCs) cultured and grown on the three-dimensional scaffold after ten days.
Figure 6C:
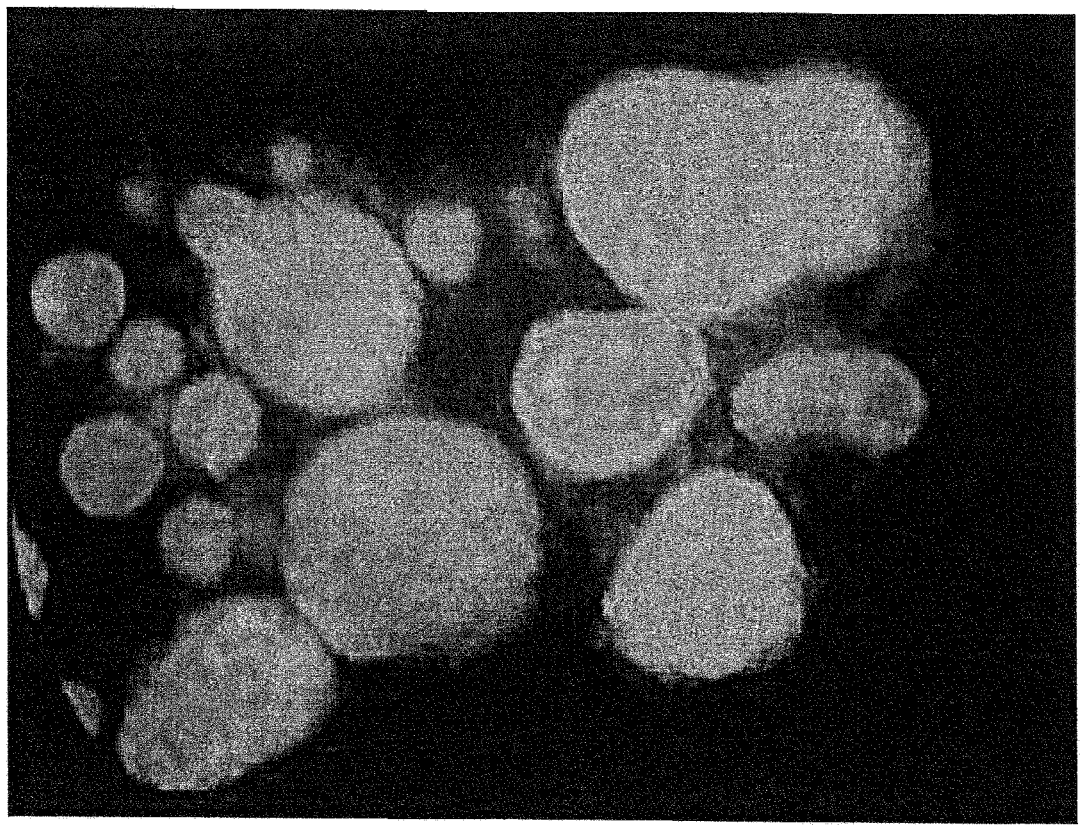
FIG. 6C is a fluorescent microscope image of the human mesenchymal stem cells (hMSCs) cultured and grown on the three-dimensional scaffold after fifteen days.
Figure 6D:
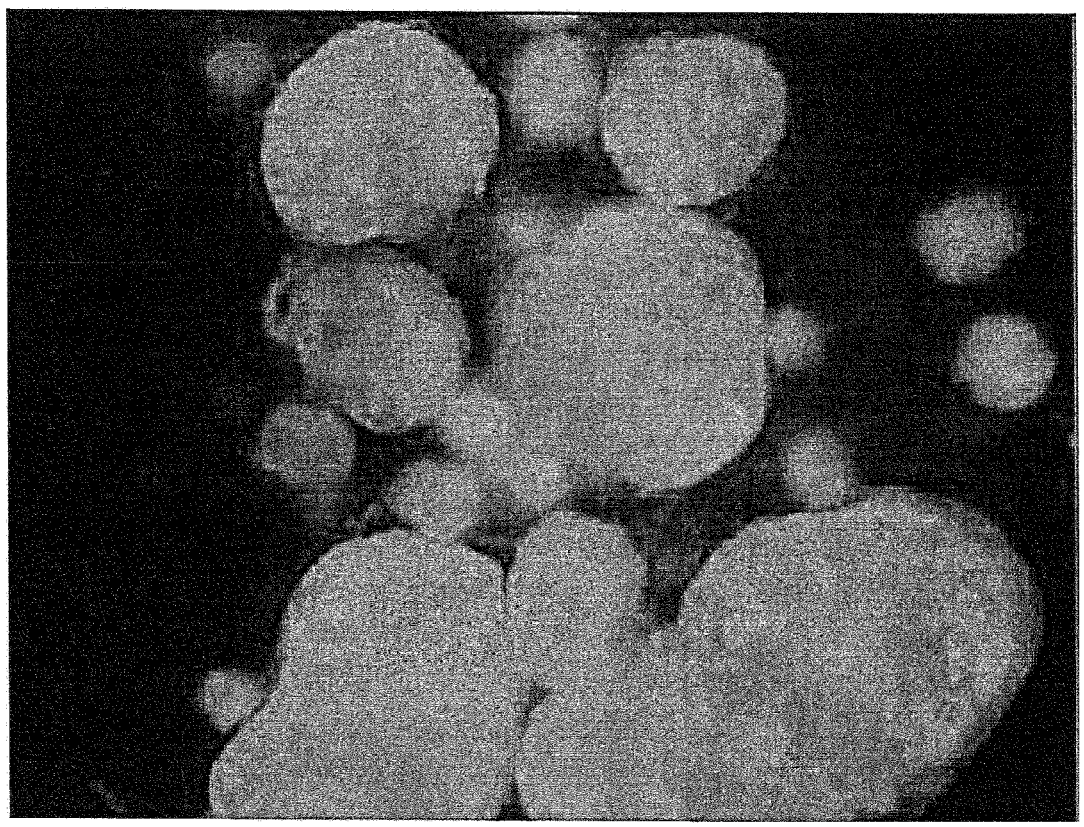
FIG. 6D is a fluorescent microscope image of the human mesenchymal stem cells (hMSCs) cultured and grown on the three-dimensional scaffold after eighteen days.

The morphology of the three-dimensional spheroid cultures was evaluated using AO/EB dual staining under fluorescence microscopy. The images illustrated the presence of healthy, normal green-colored spheroid morphology and there were no significant changes observed in the color of the spheroid morphology upon culture of hMSCs with the $BSiO_2$ constructs for 1 to 18 days. FIG. 6A shows the fluorescent microscopy image after five days; FIG. 6B shows the fluorescent microscopy image after ten days; FIG. 6C shows the fluorescent microscopy image after fifteen days; and FIG. 6D shows the fluorescent microscopy image after eighteen days. Overall, the observations of cellular functional integrity of each biosilica body, evaluation of morphology, size and number, assessment of three-dimensional culture morphology, cell adhesion and behavior, confirmed that the $BSiO_2$ microbodies are non-toxic and biocompatible with hMSCs.

It is to be understood that the present invention is not limited to the embodiments described above, but encompasses any and all embodiments within the scope of the following claims.

We claim:

1. A method of making a three-dimensional scaffold for three-dimensional cell culture, comprising the steps of:
   washing a quantity of *sorghum* husks to obtain washed *sorghum* husks;
   drying the washed *sorghum* husks to obtain dried *sorghum* husks;
   mixing the dried *sorghum* husks with hydrochloric acid to produce acid-digested *sorghum* husks;
   washing the acid-digested *sorghum* husks to remove residual hydrochloric acid;
   drying the acid-digested *sorghum* husks;
   calcining the acid-digested *sorghum* husks to produce amorphous silica residue;
   performing flux-calcination on the amorphous silica residue to produce biogenic silica microbodies; and
   clustering the biogenic silica microbodies to form the three-dimensional scaffold.

2. The method of making a three-dimensional scaffold for three-dimensional cell culture as recited in claim 1, further comprising the step of heating the dried *sorghum* husks mixed with the hydrochloric acid.

3. The method of making three-dimensional scaffold for three-dimensional cell culture as recited in claim 2, wherein the step of heating the dried *sorghum* husks mixed with the hydrochloric acid comprises heating the dried *sorghum* husks mixed with the hydrochloric acid at a temperature of approximately 120° C. for approximately 30 minutes under pressurized conditions.

4. The method of making a three-dimensional scaffold for three-dimensional cell culture as recited in claim 1, wherein the step of calcining the acid-digested *sorghum* husks is performed at a temperature of between approximately 400° C. and approximately 700° C. for a period between approximately 15 minutes and approximately 3 hours.

5. The method of making a three-dimensional scaffold for three-dimensional cell culture as recited in claim 1, wherein the step of drying the *sorghum* husks comprises drying the *sorghum* husks at a temperature of between approximately 90° C. and approximately 120° C. for a period between approximately 8 hours and approximately 12 hours.

6. The method of making a three-dimensional scaffold for three-dimensional cell culture as recited in claim 1, wherein the step of drying the acid-digested *sorghum* husks comprises drying the *sorghum* husks at a temperature of between approximately 90° C. and approximately 100° C. for a period between approximately 3 hours and approximately 4 hours.

7. The method of making a three-dimensional scaffold for three-dimensional cell culture as recited in claim 1, further comprising gradient centrifugation of the biogenic silica microbodies.

8. A method of obtaining biogenic silica microbodies from *sorghum* husks, comprising the steps of:
   washing a quantity of *sorghum* husks to obtain washed *sorghum* husks;

drying the washed *sorghum* husks to obtain dried *sorghum* husks;

mixing the dried *sorghum* husks with hydrochloric acid to produce acid-digested *sorghum* husks;

washing the acid-digested *sorghum* husks to remove residual hydrochloric acid;

drying the acid-digested *sorghum* husks;

calcining the acid-digested *sorghum* husks to produce amorphous silica residue; and performing flux-calcination on the amorphous silica residue to produce biogenic silica microbodies.

9. The method of obtaining biogenic silica microbodies from *sorghum* husks as recited in claim 8, wherein the microbodies are sinuous-shaped.

10. The method of obtaining biogenic silica microbodies from *sorghum* husks as recited in claim 8, wherein the microbodies are about 100 µm to about 1000 µm in size.

\* \* \* \* \*